United States Patent
Shirahata et al.

(10) Patent No.: US 6,475,371 B1
(45) Date of Patent: Nov. 5, 2002

(54) METHOD AND APPARATUS FOR PRODUCING ELECTROLYTIC REDUCED WATER

(75) Inventors: Sanetaka Shirahata, Fukuoka (JP); Kazumichi Otsubo, Osaka (JP)

(73) Assignee: Nihon Trim Co., Ltd., Osaka (JP)

( * ) Notice: Subject to any disclaimer, the term of this patent is extended or adjusted under 35 U.S.C. 154(b) by 0 days.

(21) Appl. No.: 09/645,350

(22) Filed: Aug. 25, 2000

(30) Foreign Application Priority Data

Sep. 1, 1999 (JP) .......................................... 11-247579

(51) Int. Cl.[7] ............................................... C02F 1/461
(52) U.S. Cl. ...................... 205/742; 205/746; 205/464
(58) Field of Search ............................... 205/742, 746, 205/464; 204/264

(56) References Cited

U.S. PATENT DOCUMENTS

| | | | |
|---|---|---|---|
| 5,578,193 A | * 11/1996 | Aoki et al. | ................. 205/746 |
| 5,593,554 A | 1/1997 | Yamanaka et al. | |
| 5,858,202 A | 1/1999 | Nakamura | ................. 205/746 |

FOREIGN PATENT DOCUMENTS

| | | |
|---|---|---|
| EP | 0 605 882 | 7/1994 |
| EP | 0 752 391 | 1/1997 |
| EP | 0 826 636 A1 | 3/1998 |
| EP | 0 826 636 | 3/1998 |
| EP | 0826636 | * 3/1998 |
| JP | 7-39877 | 2/1995 |
| JP | 10-118653 | 5/1998 |
| RU | 1188105 A | 10/1985 |

OTHER PUBLICATIONS

"*Electrochemical Activation: History, Current Situation, Perspectives*" Edited by V. M. Bakhir, pp. 10–11, 1999.

"Electrolyzed–Reduced Water Scavenges Active Oxygen Species and Protects DNA from Oxidative Damage", S. Shirahata et al., Biochemical and Biophysical Research Communications, vol. 234, No. 1, (1997), pp. 269–274 (No Month).

* cited by examiner

*Primary Examiner*—Arun S. Phasge
(74) *Attorney, Agent, or Firm*—McDermott, Will & Emery

(57) ABSTRACT

Electrolytic reduced water free of hypochlorous acid and chlorine gas is provided which is effective for cancer treatment. Water including NaOH is subjected to electrolysis. Electrolytic reduced water obtained at a cathode electrode side has been found to suppress metastasis of cancer cells. The water had no effects on growth of healthy cells during a one-week test.

3 Claims, 3 Drawing Sheets

METHOD AND APPARATUS FOR PRODUCING ELECTROLYTIC REDUCED WATER

BACKGROUND OF THE INVENTION

1. Field of the Invention

The present invention generally relates to water obtained from reduction by electrolysis (hereinafter, referred to as "electrolytic reduced water"), and more particularly, to electrolytic reduced water having an effect to inhibit metastasis of cancer cells. The present invention also relates to method and apparatus of producing such electrolytic reduced water.

2. Description of the Background Art

In recent years, mortality from cancer has been rising all over the world. A major factor of the death by cancer is remote metastasis to other organs, which in many cases has already occurred when a person is given a diagnosis of cancer.

In the current cancer treatment, however, cure is often difficult once the cancer has metastasized. Solving this problem will be a key to overcome the cancer.

Metastasis of a cancer cell takes three steps of adhesion, decomposition and invasion of the cancer cell to a basement membrane that is formed of collagen, laminin, fibronectin or the like. Activation of a group of metal catalyst, called matrix metalloprotease, by the cancer cell is known to play an important role in the metastasis. At present, chemotherapy for cancer focuses on treatment of the cancer cells already abnormal. Such therapy often exhibits insufficient effects due to the problems of selectivity, side effects and resistance with respect to the cancer. Thus, as new means for cancer treatment, an anti-cancer drug that can suppress metastasis with fewer side effects has been under development.

It is known that intracellular oxidation in various cancer cell strains is considerably greater than in normal cell strains. It has also been reported that the superoxide anion radical (hereinafter, referred to as "SAR") promotes the metastasis of cancer cells. The applicant has already proposed high concentration hydrogen dissolved water obtained by electrolysis which has potency to prevent or repair damages to DNA caused by the SAR (Japanese Patent Laying-Open No. 10-118653 (U.S. Ser. No. 08/917,336)).

To produce such high concentration hydrogen dissolved water (i.e., electrolytic reduced water) applicable to cancer treatment, tap water has been electrolyzed with NaCl dissolved therein as electrolysis promoting catalyst. This method has an advantage that it is possible to obtain not only the electrolytic reduced water (at the cathode side), but also bactericidal water having an oxidizing property at the anode side. However, the method also poses a problem that, at the time of electrolysis of the NaCl solution, hypochlorous acid and chlorine gas are produced in large amounts and dissolve into the electrolytic reduced water. Water containing hypochlorous acid and chlorine gas is unsuitable for drinking and considered being carcinogenic. Thus, the conventional method is unable to produce electrolytic reduced water highly effective in cancer treatment.

SUMMARY OF THE INVENTION

The present invention is directed to solve the above-mentioned problems. A main object of the present invention is to provide electrolytic reduced water completely free of hypochlorous acid and chlorine gas that is applicable to cancer treatment.

Another object of the present invention is to provide a method of producing such electrolytic reduced water.

Yet another object of the present invention is to provide an apparatus for producing such electrolytic reduced water.

In general, electrolytic water is obtained by electrolyzation of water, both in cathode and anode chambers. The electrolytic reduced water described herein, however, does not refer to all such electrolytic water. Reduction only takes place in the cathode chamber, and therefore, the reduced water is obtained only in the cathode chamber. Thus, the electrolytic reduced water disclosed in the present invention can be defined as water which has been reduced by electrolysis in the cathode chamber and has its oxidation-reduction potential of a negative value.

The electrolytic reduced water according to a first aspect of the present invention is obtained by electrolyzing water including NaOH therein.

As such NaOH solution is completely free of chlorine, the electrolysis of the solution produces neither hypochlorous acid nor chlorine gas.

In the electrolytic reduced water according to a second aspect of the present invention, the concentration of NaOH is selected within a range from 0.0001N to 0.02N.

If bubbles are vigorously produced during electrolysis, atomic hydrogen or hydrogen radicals themselves are also coupled to form hydrogen gas and escape from within the water. Thus, in the electrolysis accompanied by such intense bubbling, the amount of hydrogen radicals dissolved in the electrolytic reduced water (refined liquid at the cathode side) is unlikely to increase from a fixed amount. Therefore, it is desirable that the least possible amount of bubbles is produced during the electrolysis to attain a larger amount of dissolved hydrogen. By selecting the NaOH concentration within the range from 0.0001N to 0.02N, substantially no bubbles are generated during the electrolysis, and thus, it is possible to obtain stable electrolytic reduced water.

In addition, by selecting the NaOH concentration within this range, it is possible to cause electrolytic reaction approximately at the same level as in the case of tap water.

In the electrolytic reduced water according to a third aspect of the present invention, the concentration of NaOH is selected within the range from 0.0001N to 0.002N.

By selecting the NaOH concentration within this range, electrolytic reduced water with an increased amount of hydrogen dissolved therein can be obtained.

The electrolytic reduced water according to a fourth aspect of the present invention includes a hydrogen radical.

The electrolytic reduced water according to a fifth aspect of the present invention is electrolytic reduced water including a hydrogen radical that is obtained by electrolyzing water containing NaOH.

The electrolytic reduced water according to a sixth aspect of the present invention is an anti-cancer drug made of a water solution containing a hydrogen radical.

The electrolytic reduced water according to a seventh aspect of the present invention is obtained by electrolyzing water containing NaOH, which has an oxidation-reduction potential of at most −50 mV, a dissolved oxygen amount of at most 9.5 ppm and a dissolved hydrogen amount of at least 300 ppb.

In the method of producing electrolytic reduced water according to an eighth aspect of the present invention, a water solution containing NaOH is first introduced into both a cathode chamber and an anode chamber that are separated by a diaphragm. With a cathode electrode being immersed in the cathode chamber and an anode electrode immersed in the anode chamber, electricity is applied between the cathode electrode and the anode electrode to electrolyze the water solution containing NaOH. Electrolytic reduced water is obtained in the cathode chamber, which is drawn out therefrom.

According to the method, the NaOH solution is used as electrolyte, which is free of chlorine. Therefore, it is possible to obtain electrolytic reduced water completely free of hypochlorous acid and chlorine gas.

In the method of producing electrolytic reduced water according to a ninth aspect of the present invention, the electrolysis is effected with the cathode and anode chambers both being sealed.

Accordingly, it is possible to suppress generation of hydrogen gas while conducting the electrolysis, thereby increasing the amount of dissolved hydrogen.

In the method of producing electrolytic reduced water according to a tenth aspect of the present invention, the electrolysis is conducted with voltage, current and time that are selected such that no hydrogen gas is generated from the cathode chamber.

Accordingly, cathode water having a large amount of dissolved hydrogen can be obtained in the cathode chamber.

The apparatus for producing electrolytic reduced water according to an eleventh aspect of the present invention includes: filter means for filtrating raw water to produce clear water; NaOH add means for adding a NaOH solution to the clear water filtrated by the filter means; and an electrolysis tank having cathode and anode chambers separated by a diaphragm, to which the clear water having the NaOH solution added therein is introduced.

As the apparatus is provided with the NaOH add means, it is possible to electrolyze the water solution including NaOH, producing neither hypochlorous acid nor chlorine gas.

In the apparatus for producing electrolytic reduced water according to a twelfth aspect of the present invention, a first conduit is provided between the NaOH add means and the electrolysis tank to introduce the clear water with the NaOH solution to the electrolysis tank. A second conduit is connected to the electrolysis tank, which draws cathode water discharged from the cathode chamber outwards. A third conduit is connected to the electrolysis tank to draw anode water discharged from the anode chamber outwards. First, second and third valves are provided in the first, second and third conduits, respectively, to open/close the relevant conduits. The apparatus also includes means for controlling opening/closing of the first, second and third valves.

According to the apparatus, it is possible to perform electrolysis with the cathode and anode chambers being sealed by closing the first, second and third valves. This enables production of the cathode water containing a large amount of dissolved hydrogen.

The electrolytic reduced water according to a thirteenth aspect of the present invention is obtained in the cathode chamber.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Hereinafter, embodiments of the present invention will be described.

Figure 1:
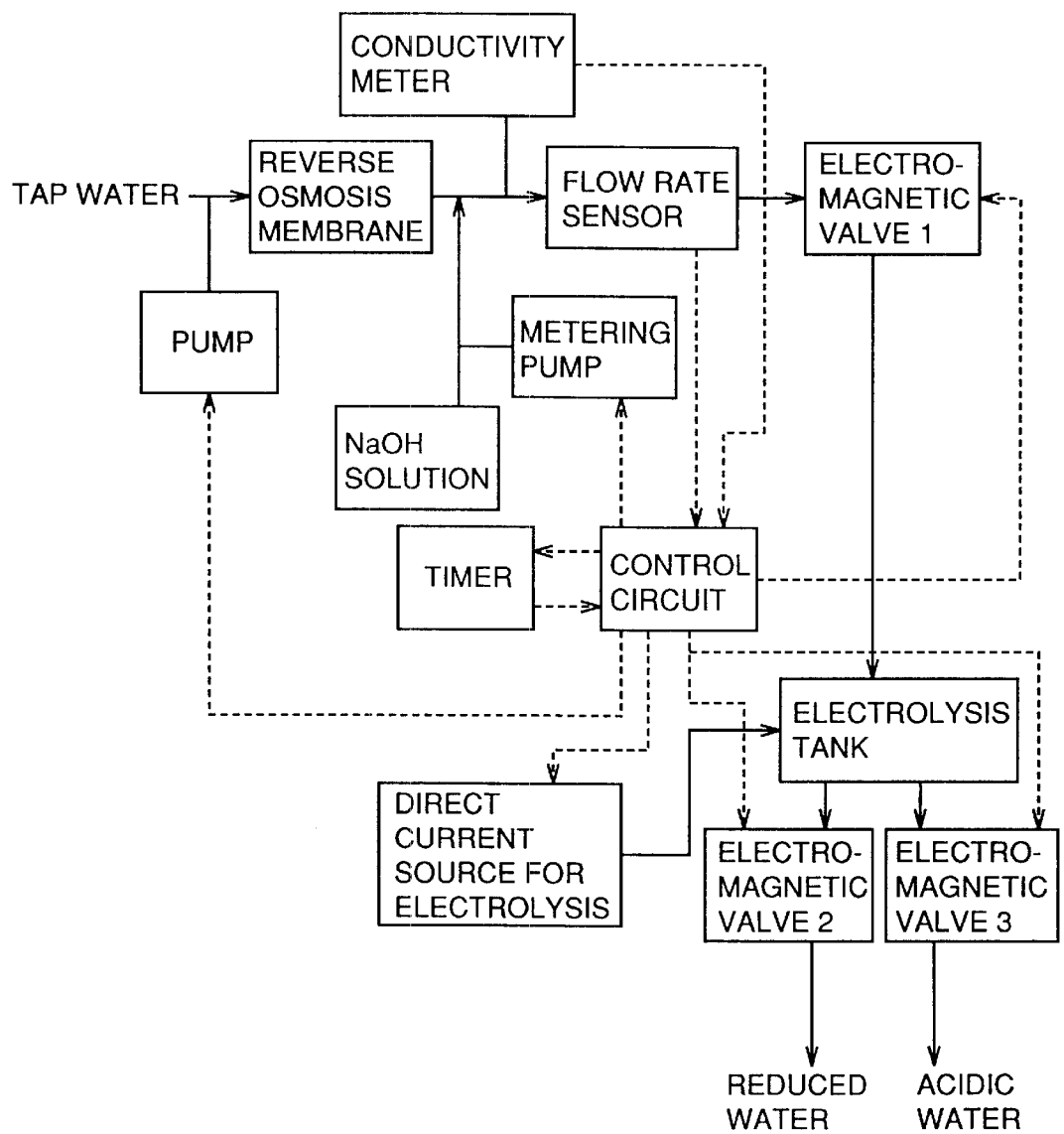
FIG. 1 is a diagram showing a NaOH solution electrolyzing system according to the present invention.

FIG. 1 schematically shows an apparatus for producing electrolytic reduced water free of hypochlorous acid and chlorine gas that is effective for cancer treatment. Specifically, FIG. 1 illustrates a NaOH solution electrolyzing system.

Referring to FIG. 1, raw water (tap water) is pressurized by a pump and filtrated by a reverse osmosis membrane to obtain purified water. A NaOH solution is added to the purified water via a metering pump. The metering pump is controlled to achieve a prescribed concentration by measuring electrical conductivity of the solution. The NaOH solution is supplied to an electrolysis tank through a flow rate sensor and an electromagnetic valve 1. Once the electrolysis tank is filled with the NaOH solution, the flow rate becomes 0, and a stop signal is supplied from the flow rate sensor to a control circuit. In response to the stop signal supplied, the pump and the metering pump stop, and electromagnetic valve 1 is closed. A timer is activated, and a direct current for use in electrolysis is supplied to the electrolysis tank for a prescribed time period. When the time is up, electromagnetic valves 2 and 3 are opened to draw out reduced water and acidic water produced respectively. After the produced water is drawn out, each electromagnetic valve attains its initial state, and the NaOH solution is supplied for next electrolysis.

Figure 2:
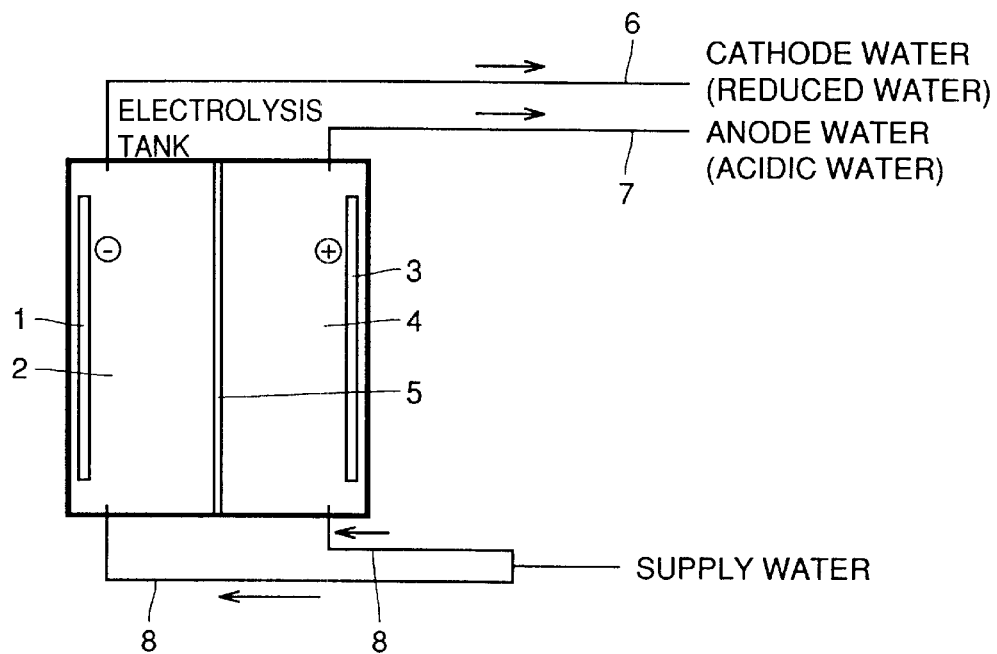
FIG. 2 is a diagram showing an electrolysis tank according to the present invention.

FIG. 2 schematically shows the electrolysis tank. The electrolysis tank includes a cathode chamber 2 containing a cathode electrode 1, and an anode chamber 4 containing an anode electrode 3. Chambers 2 and 3 are separated by a diaphragm 5. A cathode water outlet pipe 6 is connected to cathode chamber 2 to draw out the cathode water (the electrolytic reduced water). A drain pipe 7 is connected to anode chamber 4 to discharge the anode water (the acidic water) outwards. Feed pipes 8 are connected to cathode chamber 2 and anode chamber 4, respectively, to supply them with purified water having NaOH of a prescribed amount added therein.

EXAMPLE 1

Using purified water filtered through a reverse osmosis membrane or the like, 0.01% NaOH solution was prepared and subjected to electrolysis. Electrolytic reduced water was obtained completely free of hypochlorous acid and chlorine gas, since the NaOH solution was used.

When electrolyzing water, oxygen gas is generated at the anode side and hydrogen gas at the cathode side. The hydrogen gas is generated because a hydrogen ion produced by the electrolysis and an electron supplied from the cathode electrode are coupled to form atomic hydrogen, and two hydrogen atoms are then coupled to form hydrogen gas. As will be described later, the electrolytic reduced water thus obtained has potency to prevent or suppress growth and metastasis of cancer cells, which is considered attributable to strong antioxidation property of the atomic hydrogen. Therefore, it is desirable that a large amount of hydrogen in its atomic state is dissolved in water. In the cathode water obtained from high current electrolytic reaction utilizing high voltage, hydrogen tends to be gasified for the most part, thereby reducing the dissolved amount of atomic hydrogen. To avoid such phenomena, it is preferable to perform the electrolysis over a long period of time under the condition that can prevent generation of hydrogen gas. In other words, the electrolysis is preferably conducted under low voltage and low current over a long period of time. It was found that the electrolytic reduced water could be obtained without generating hydrogen gas if the NaOH solution was electrolyzed under the conditions of a voltage from 5V to 100V, a current from 5 mA to 2 A, and a time period from 5 to 120 minutes. The obtained electrolytic reduced water exhibited pH of 11.5 and ORP (oxidation-reduction potential) of −850 mv.

Here, the oxidation-reduction potential was measured at room temperature employing an "oxidation-reduction potential meter" available from Toa Electronics (Toa Denpa Kogyo), by immersing its electrodes for measurement into the test water.

The characteristics of the obtained electrolytic reduced water are shown in Tables 1 and 2.

The results shown in Tables 1 and 2 are similar to each other, but they were measured on different days taking different water samples. The comparison of the tables showed that it was possible to obtain data exhibiting good reproducibility.

Table 3 shows conditions of electrolysis, i.e., current density values, corresponding to electrolyzed degrees 1–5. The current density of tap water is expressed as 0.0 mA/cm$^2$, because it has undergone no electrolysis. The current density, which is controlled by a microcomputer, is one of the most important conditions of electrolysis. Once the current density is determined, the voltage and the NaOH concentration are consequently determined.

In Tables 1 and 2, the amounts of dissolved oxygen were measured using a dissolved oxygen meter of DO-14P type available from Toa Electronics (Toa Denpa Kogyo). The amounts of dissolved hydrogen were measured using a dissolved hydrogen meter of DHD1-1 type also available from Toa Electronics.

Tables 1 and 2 also include the results showing presence/absence of hydrogen radicals. x shows that hydrogen radicals were not included; O shows that hydrogen radicals were included. The presence/absence of hydrogen radicals (atomic hydrogen) was confirmed utilizing a characteristic of tungsten oxide (in the form of plate). Tungsten oxide has potency to adsorb hydrogen radicals in a specific manner, and it turns blue when adsorbing the hydrogen radicals. The obtained electrolytic reduced water was made contact with tungsten oxide to qualitatively determine the presence/absence of hydrogen radicals.

EXAMPLE 2

The evaluation results of cancer cell metastasis inhibiting effects of the obtained electrolytic reduced water (with electrolyzed degree of 5 in Table 1) will be described.

Figure 3:
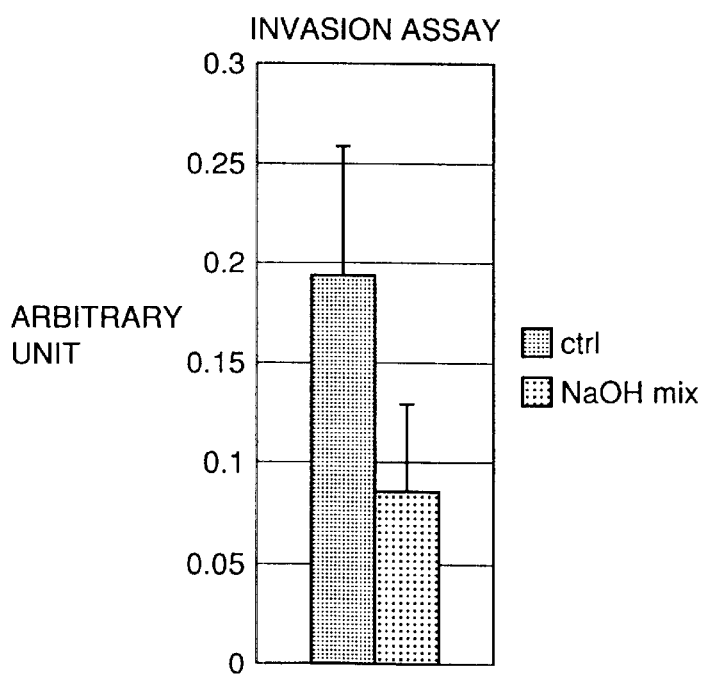
FIG. 3 illustrates a cancer cell metastasis inhibiting effect exhibited by NaOH electrolytic reduced water.

FIG. 3 shows the inhibiting effects of the electrolytic reduced water against highly metastatic human fiber sarcoma cell strains HT1080 in a metastasis model system in vitro. Here, HT1080 cells available from a cell bank (e.g., JCRB Cell Bank or ATCC (in U.S.A.)) were employed.

The HT1080 cells were cultured in 10% fetal bovine serum added MEM medium at a temperature of 37° C. under 5% $CO_2$/95% air environment. A chemotaxel filter (pore size: 8 μm) was coated with matrigel of 25 μg/filter. Sub-confluent HT1080 cells were suspended in the MEM medium containing 0.1% bovine serum albumin (BSA) and the number of cells was adjusted to $4\times10^5$/ml. 200 μl of the resultant was added to a chamber in its upper room. Immediately after addition of the cells, 700μ of the MEM (Minimum Essential Medium; medium including the least possible amount of nutritious ingredients) containing 10 μg/ml of fibronectin was added to the chamber in its lower room (having a 24 holes plate) (a 24 holes plate side), and cultured in a $CO_2$ incubator. After six hours have passed, the chamber was taken out. Cells were removed from the upper surface of the filter with a cotton bud, and moved to the 24 holes plate containing WST-1 (an indicator that changes its color depending on metabolic ability specific to living cells, or the number of living cells). After culture for 16 hours, absorbance at 450 nm was measured. Referring to FIG. 3, "ctrl" represents the result when purified water was used, and "NaOH mix" represents the result when the electrolytic reduced water obtained with electrolyzed degree of 5 in Table 1 was used. As seen from FIG. 3, invasive metastasis of HT1080 cells is dramatically reduced in the case of NaOX mix compared to the case of ctrl. This means that the electrolytic reduced water has suppressed the invasive metastasis of the human fiber sarcoma cells.

Figure 4:
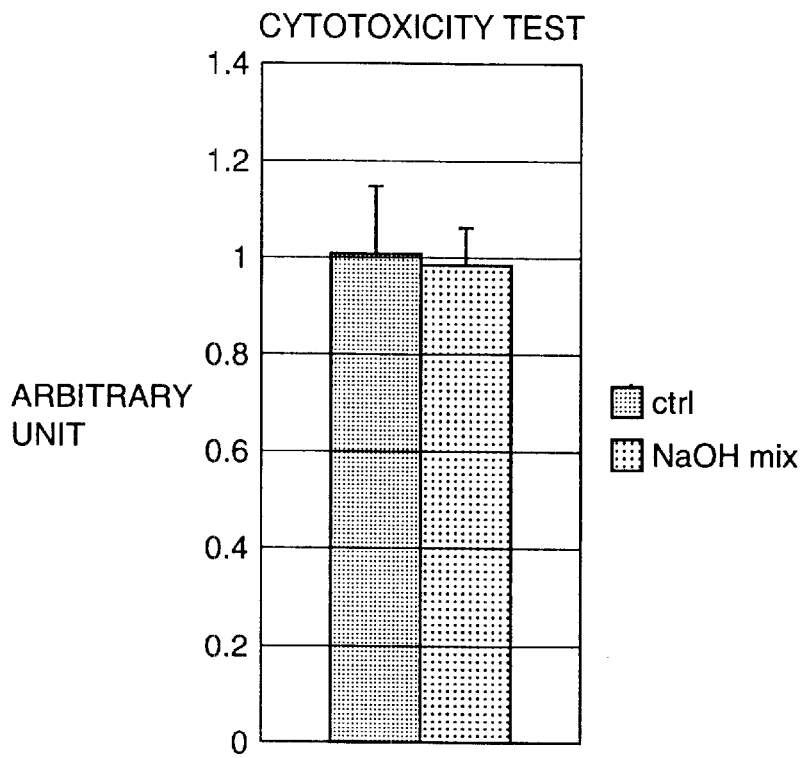
FIG. 4 illustrates the result of a cytotoxicity test of the NaOH electrolytic reduced water.

FIG. 4 illustrates the result of one-week cytotoxicity test. HT1080 cells were cultured in 10% fetal bovine serum

TABLE 1

| | water temperature (° C.) | pH | oxidation-reduction potential (mV) | dissolved oxygen amount (ppm) | dissolved hydrogen amount (ppb) | presence/absence of H radical |
|---|---|---|---|---|---|---|
| tap water reduced water | 13.1 | 7.5 | +652 | 10.0 | 2.3–2.6 | x |
| ED: 1 | 12.7 | 9.8 | −94 | 9.4 | 400–450 | o |
| ED: 2 | 13.2 | 10.3 | −247 | 8.6 | 690–720 | o |
| ED: 3 | 13.2 | 10.4 | −494 | 8.2 | 880–900 | o |
| ED: 4 | 13.7 | 10.7 | −729 | 7.2 | 1030–1060 | o |
| ED: 5 | 14.0 | 11.5 | −850 | 6.8 | 1090–1130 | o |

ED: electrolyzed degree added MEM medium that had been prepared using purified water or the electrolytic reduced water (with electrolyzed degree of 5). After culture for one week, WST-1 was added, and the number of living cells was measured with absorbance at 450 nm. No significant difference was found between the result obtained using purified water (ctrl) and the result obtained using the electrolytic reduced water (NaOH mix). This means that the electrolytic reduced water has no adverse effects on growth of healthy cells. Thus, from the results shown in FIGS. 3 and 4, it has become clear that the NaOH electrolytic reduced water is capable of suppressing the invasive metastasis activity without introducing cytotoxicity.

Figure 5:
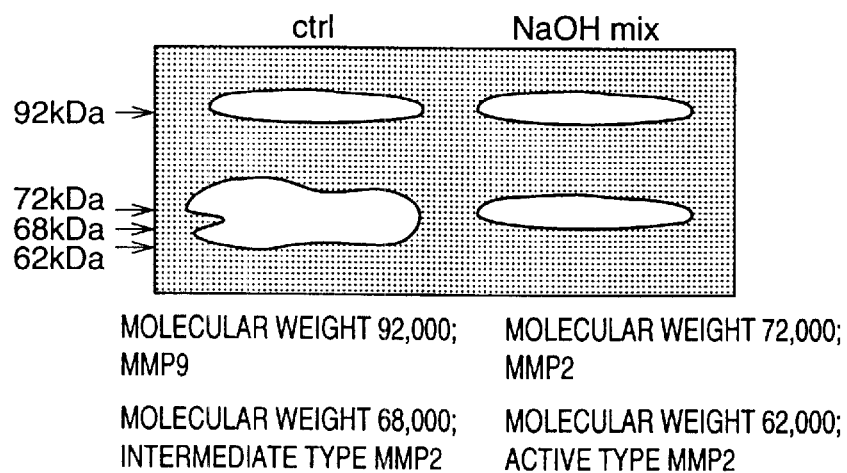
FIG. 5 illustrates the result of analysis of gelatinase/IV type collagenase activity by zymography.

Referring to FIG. 5, matrix metalloprotease (MMP) playing an important role in the metastasis of cancer cells was analyzed, focusing on MMP2 and MMP9 among others, which are known as being particularly deeply involved in the cancer metastasis.

FIG. 5 illustrates the analysis result of gelatinase/IV type collagenase activity in zymography. Specifically, HT1080 cells were cultured on a chemotaxel chamber for 48 hours, and then the supernatant of the cultured cells was purified using a centrifugal device before recovery. 12 $\mu$l of the supernatant was added to 10% polyacryl-amide gel containing 1 mg/ml of gelatin. After gel electrophoresis, the gel was washed with 2% Triton X-100 for one hour and kept at 37° C. for 60 hours. Thereafter, the gel was dyed with 0.1% Ponceau S to detect gelatinase activity, which was represented as a white band on a colored background. In FIG. 5, the wider the white band, the greater the activity of MMP promoting the metastasis of cancer cells.

The result of the analysis showed that the NaOH electrolytic reduced water had no effects on manifestation of MMP2 and MMP9, but it significantly suppressed activation of MMP2.

From the results as described above, it has become clear that the NaOH electrolytic reduced water has cancer cell metastasis inhibiting effects by suppressing the activation of MMP2.

Inhibiting the metastasis mechanism of cancer cells is important not only for preventing the metastasis itself, but also for suppressing vascularization due to the invasive activity of the cancer cells as well as for preventing the cancer cells from becoming malignant. Further, a drug for inhibiting the cancer metastasis must maintain its effects for a long period of time and have the least possible side effects. In the present invention, it has been proved that the NaOH electrolytic reduced water can suppress the metastasis of cancer cells without damaging the cells. This suggests a possibility that utilizing such water daily as drinking water may prevent progress of the cancer, and thus, it is considered to have a great significance for cancer treatment in the future.

As explained above, the electrolytic reduced water obtained by the present invention is a kind of water exhibiting an antioxidation property and containing no oxide such as hypochlorous acid and chlorine gas, which is not only applicable to medical treatment but also suitable for drinking and other uses.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of producing electrolytic reduced water, comprising the steps of:

introducing a water solution including NaOH within a concentration range of from 0.0001 N to 0.02 N to both a cathode chamber and an anode chamber separated by a diaphragm;

applying electricity between a cathode electrode immersed in said cathode chamber and an anode electrode immersed in said anode chamber to perform electrolysis of said water solution including NaOH wherein said electrolysis is performed with said anode and cathode chambers sealed; and drawing out electrolytic reduced water obtained at said cathode chamber.

2. The method of producing electrolytic reduced water according to claim 1, wherein said electrolysis is performed with voltage, current and time selected to prevent generation of hydrogen gas from said cathode chamber.

3. An apparatus for producing electrolytic reduced water, comprising:

filter means for filtrating raw water to produce clear water;

NaOH add means for adding a NaOH solution to the clear water filtrated by said filter means;

an electrolysis tank having a cathode chamber and an anode chamber separated by a diaphragm for introducing therein the clear water with said NaOH solution added thereto;

a first conduit provided between said NaOH add means and said electrolysis tank for introducing said clear water with said NaOH solution added thereto to said electrolysis tank;

a second conduit connected to said electrolysis tank for drawing cathode water discharged from said cathode chamber outwards;

a third conduit connected to said electrolysis tank for drawing anode water discharged from said anode chamber outwards;

a first valve provided within said first conduit for opening/closing said first conduit;

a second valve provided within said second conduit for opening/closing said second conduit;

a third valve provided within said third conduit for opening/closing said third conduit; and control means for controlling opening/closing of said first, second and third valves.

\* \* \* \* \*